United States Patent [19]
Ishii et al.

[11] Patent Number: 5,965,651
[45] Date of Patent: *Oct. 12, 1999

[54] LIQUID-ABSORBING MATERIAL COMPOSITION, MOLDED PRODUCT THEREFROM, PROCESS FOR PREPARING THE SAME AND USE THEREOF

[75] Inventors: Tetsuya Ishii; Tetsuhiko Yamaguchi, both of Kawasaki, Japan

[73] Assignee: Showa Denko K.K., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/755,228

[22] Filed: Nov. 22, 1996

[51] Int. Cl.$^6$ ........................................ C08K 5/05
[52] U.S. Cl. .......................... 524/388; 524/104; 524/108; 524/113; 524/173; 524/205; 524/233; 524/234; 524/235; 524/315; 524/364; 524/376; 524/377; 524/379; 524/386; 524/387; 524/389; 524/502; 524/507; 524/512; 524/529; 524/555; 524/535
[58] Field of Search ....................... 524/388, 379, 524/555, 104, 108, 113, 173, 233, 205, 234, 235, 315, 364, 376, 377, 386, 387, 389, 502, 507, 512, 529, 535

[56] References Cited

U.S. PATENT DOCUMENTS

| | | | |
|---|---|---|---|
| 5,338,815 | 8/1994 | Aizawa et al. | 524/555 |
| 5,401,695 | 3/1995 | Wu | 524/556 |
| 5,407,996 | 4/1995 | Aizawa et al. | 524/555 |

FOREIGN PATENT DOCUMENTS

| | | |
|---|---|---|
| 52-143710 | 11/1977 | Japan . |
| 56-79122 | 6/1981 | Japan . |
| 678402 | 11/1988 | Japan . |
| 1103643 | 4/1989 | Japan . |

*Primary Examiner*—Judy M. Reddick
*Attorney, Agent, or Firm*—Sughrue, Mion, Zinn, Macpeak & Seas, PLLC

[57] ABSTRACT

A liquid-absorbing material composition containing a crosslinking agent (component A), N-vinylcarboxamide copolymer (component B) having a functional group capable of crosslinking with the component A, water (component C), a water-soluble organic solvent (component D) and a plasticizer (component E), a molded liquid-absorbing material prepared from the composition, a method of manufacturing the molded liquid-absorbing material, and uses thereof are provided. The liquid-absorbing material composition has a high flowability, and gives a uniform continuous layer so that it can be directly molded readily into film- or sheet-shaped molded liquid-absorbing material without requiring secondary processing as in the case of conventional water-absorbing polymer. Use of the liquid-absorbing material composition allows manufacture in short time of molded products which are excellent in liquid-absorbing performance that can be utilized as a freshness retaining agent, a moisture-conditioning agent, an agricultural and horticultural water-retaining sheet, a soil improving agent, an anti-dewing agent, sanitary goods, a waste liquid solidifying material, a water preventing sheet, a water running preventing shielding material, a pharmaceutical, a medical tool, a humectant or desiccant.

12 Claims, No Drawings

LIQUID-ABSORBING MATERIAL COMPOSITION, MOLDED PRODUCT THEREFROM, PROCESS FOR PREPARING THE SAME AND USE THEREOF

FIELD OF THE INVENTION

This invention relates to a liquid absorbing-material composition, a molded product from the composition, process for preparing the molded product and use of the molded product. More particularly, this invention relates to a liquid-absorbing material composition that absorbs efficiently not only water but also ionic aqueous solutions, aqueous solutions containing certain organic solvents, and alcohols, shows an improved gel strength after it absorbs liquids and has such a flexibility that it is easily molded into various shapes such as a film, sheet, and the like.

BACKGROUND OF THE INVENTION

It is well known that water-absorbing polymers have various utilities and have been used in various applications such as hygienic supplies (sanitary goods, diapers, etc.), agricultural and horticultural equipment (water-retaining agent) and those applications which require water-retaining properties.

As the water-absorbing polymers, various polymers have been known, such as starch-based polymers, poval-based polymers, cellulose-based polymers and the like. Among these, however, secondary products obtained by processing powdery or fibrous materials are efficiently put to practical use. More particularly, in the absence of suitable plasticizers, conventional water-absorbing polymers by themselves have not been able to be molded into the shape of a sheet or the like. For example, powdery materials have to be carried on a fibrous base material such as paper or nonwoven fabric before molding (e.g., Examined Publication No. 6-78402, Japanese Patent Application Laid-Open No. 52-143710, etc.). In such molded products from carried powdery water-absorbing polymer, the water-absorbing sites are water-absorbing polymer which are scattered or dotted in the molded product and, hence, the molded products show only a limited water absorbency and has a low liquid absorbency for ionic and water-soluble organic solvent-containing solutions. Furthermore, the molded products are complicated and costly to manufacture.

To solve the above-described problems, there has been disclosed a method for preparing a film- or fiber-shaped water-absorbing composition using a hydrophilic polymer obtained by copolymerizing carboxyl group-containing monomers (cf., Japanese Patent Application Laid-Open No. 1-103643, and Japanese Patent Application laid-Open No. 56-79122). However, no suitable plasticizer therefor was available and the films obtained were so hard and brittle that they were not put into practical use for some applications. On the other hand, Japanese Patent Application Laid-Open No. 1-103643 discloses a method in which polyvinyl alcohol and a carboxyl group-containing copolymer are used as a hydrophilic polymer and polyhydric alcohol is used as a plasticizer. This method, however, has a problem that the polyvinyl alcohol bleeds out after absorbing the liquid since the polyvinyl alcohol and the alcohol do not have sufficient affinity for each other and the polyvinyl alcohol does not participate in crosslinking. Further, in order to obtain by the technique a liquid (sol form) which is flexible enough to be molded, it is necessary to dilute the composition with water and, as a result, to vaporize the water upon molding, so that the manufacture of a molded product has taken considerable time.

Therefore, an object of this invention is to provide a composition which is free of the problems encountered by the conventional water-absorbing molded products containing a liquid-absorbing polymer in a dispersed state, i.e., a liquid-absorbing material composition which has an improved water absorbency so that every part of the composition can absorb water.

Another object of this invention is to provide a liquid-absorbing material composition that has an elevated liquid-absorbing efficiency for ion-containing water, water-soluble organic solvent-containing liquid or alcohols.

Still another object of this invention is to provide a liquid-absorbing material composition having flexibility so that it can easily be molded into a sheet or the like and an improved gel strength after absorbing a liquid.

Yet another object of this invention is to provide a molded product of liquid-absorbing material comprising such a liquid-absorbing material composition crosslinked to have any desired shape and a method for manufacturing such a molded product.

Further, an object of this invention is to provide various uses of such a molded product of liquid-absorbing material.

SUMMARY OF THE INVENTION

In order to solve the above-described problems, the present inventors have investigated intensively and as a result, it has now been found that a simple composition comprising a crosslinking agent (component A), an N-vinylcarboxamide copolymer (component B) having a functional group which reacts with the crosslinking agent, water (component C), a water-soluble organic solvent (component D) and a plasticizer (component E) as essential components, when the contents of component C and the like are selected appropriately, becomes a composition which has a high flowability and can form a uniform continuous layer so that it has a remarkably improved moldability, that crosslinking the composition after or during molding can easily give rise to a molded product (gel) of liquid-absorbing material in the shape of a sheet or the like having excellent shape-retaining properties, that the molded product thus obtained has an excellent liquid absorbency and can absorb not only water but also ion-containing aqueous solutions, aqueous solutions of certain organic solvents, and alcohols, and that the gel after liquid absorption has a sufficient strength (shape retaining properties) and flexibility and is excellent in liquid retaining properties. This invention has been completed based on the discoveries.

The liquid absorbing material composition according to this invention is unique in that it can be processed into a molded product of liquid absorbing material in the shape of a sheet or the like without resort to a complicated process as in the case of the conventional powdery or fibrous water-absorbing polymer gel.

DETAILED DESCRIPTION OF THE INVENTION

This invention provides the following liquid-absorbing material composition, a molded product of liquid-absorbing material prepared by molding the composition, a method of manufacturing the molded product and uses of the molded product.

1) A liquid-absorbing material composition comprising a crosslinking agent (component A), an N-vinylcarboxamide copolymer (component B) having a functional group which reacts with the component A, represented by formula (IA):

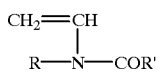

(IA)

wherein R represents a hydrogen atom or an alkyl group having 1 to 4 carbon atom(s) and R' represents an alkyl group having 1 to 4 carbon atom(s), water (component C), a water-soluble organic solvent (component D), and a plasticizer (component E).

2) The liquid-absorbing material composition as described in 1) above, further containing a hydrophilic polymer (component F) which does not react with the crosslinking agent (component A).

3) The liquid-absorbing material composition as described in 1) above, wherein the proportion of the crosslinking agent (component A) to the N-vinylcarboxamide copolymer (component B) is 0.01 to 90% by weight of the component A: 10 to 99.99% by weight of the component B, wherein the amount of the water (component C) is 10 to 65% by weight based on the total weight of the composition and the amount of the water-soluble organic solvent (component D) is 10 to 90% by weight based on the total weight of the composition.

4) The liquid-absorbing material composition as described in 1) above, wherein the crosslinking agent (component A) is selected from at least one of polyfunctional epoxy compounds, aldehydes, N-methylols, dicarboxylic acids, epichlorohydrin, boric acid, diamines, diols, bisepoxides, and diisocyanates.

5) The liquid-absorbing material composition as described in 1) above, wherein the N-vinylcarboxamide copolymer (component B) has at least one functional group selected from a hydroxyalkyl group, a carboxyl group, a sulfonic acid group, a phosphoric acid group, an aminocarbonyl group, a mono- or di-lower alkylaminocarbonyl group, an amino group, a mono- or dialkylamino group.

6) The liquid-absorbing material composition as described in 1) above, wherein the N-vinylcarboxamide copolymer (component B) substantially comprises a repeating unit represented by general formula (I):

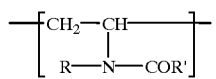

(I)

wherein R represents a hydrogen atom or an alkyl group having 1 to 4 carbon atom(s) and R' represents an alkyl group having 1 to 4 carbon atom(s); general formula (II):

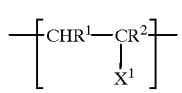

(II)

wherein $R^1$ represents a hydrogen atom or a carboxyl group or its alkali salts, $R^2$ represents a hydrogen atom, a methyl group or a carboxyl group or its alkali salts, $X^1$ represents a carboxyl group or its alkali salts, or $R^1$ and $X^1$ taken together with the carbon atoms to which they are attached form a cyclic acid anhydride structure; general formula (III):

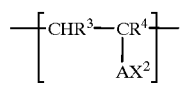

(III)

wherein $R^3$ and $R^4$ independently represent a hydrogen atom, a $C_1$~$C_4$-alkyl group or a carboxyl group or its alkali salts, A is a group represented by general formula (V), (VI) or (VII):

(V)

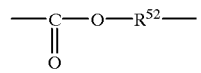

(VI)

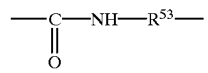

(VII)

wherein $R^{51}$, $R^{52}$ and $R^{53}$ independently represent a C1~C10-straight chain or branched alkylene group, $X^2$ represents a carboxyl group, a phosphoric group or their alkali salts, or $R^3$ and $X^2$ taken together with the carbon atoms to which they are attached form a cyclic acid anhydride structure; and/or general formula (IV):

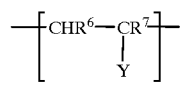

(IV)

wherein $R^6$ and $R^7$ independently represent a hydrogen atom or a C1~C4-alkyl group, Y represents a C1~C4-hydroxyalkyl group, —$CH_2NR^8R^9$ ($R^8$ and $R^9$ independently represent a hydrogen atom, a C1~C4-alkyl group or a C1~C4-alkenyl group), —$COOR^{10}$ ($R^{10}$ represents a C1~C4-alkyl group or a C1~C4-hydroxyalkyl group), —$CONR^{11}R^{12}$ ($R^{11}$ and $R^{12}$ independently represent a hydrogen atom, a C1~C4-alkyl group, a C3~C5-alkenyl group or a methylol group), —CONH—$R^{13}$—$NR^{14}R^{15}$ ($R^{13}$ represents a simple chemical bond or the same group as defined by A above, and $R^{14}$ and $R^{15}$ independently represent the same groups as $R^{11}$ and $R^{12}$ above), or their quaternary ammonium salts, or a phenyl group substituted with 1 to 3 hydroxyl groups at the nucleus thereof, with the repeating unit (I) occupying 99.99 to 50% by weight, repeating units (II), (III) and/or (IV) occupying 0.01 to 50% by weight.

7) The liquid-absorbing material composition as described in 6) above, wherein R is a hydrogen atom and R' is a methyl group in general formula (I) which represents the repeating unit of the N-vinylcarboxamide copolymer (component B).

8) The liquid-absorbing material composition as described in 1) above, wherein the plasticizer (component E) is a polyhydric alcohol.

9) A molded product of liquid-absorbing material obtained by molding the composition as described in 1) above.

10) The molded product of liquid-absorbing material as described in 9) above, molded into any one of film-, sheet-, powder-, flake- and fiber-like shapes.

11) A method of manufacturing a molded product of liquid-absorbing material, comprising vaporizing the water (component C) and the water-soluble organic solvent (component D) from the composition as described in 1) above.

12) Use of the molded product of liquid-absorbing material as described in 9) above as a freshness-retaining agent, a moisture-conditioning agent, an agricultural and horticultural water-retaining sheet, a soil improving agent, an anti-dewing agent, sanitary goods, a waste liquid solidifying material, a water preventing sheet, a water running preventing shielding material, a pharmaceutical, a medical tool, a humectant or desiccant.

The N-vinylcarboxamide which constitutes the copolymer component (component B) has an amide group, i.e., a hydrophilic group, and an alkyl group having 1 to 4 carbon atoms, i.e., an lipophilic group, in one molecule. Presence of the alkyl group allows the component B to exhibit affinity for alcohols and makes it possible to use alcohols as a plasticizer. Further, this makes it possible to use certain water-soluble organic solvents in diluting (decreasing the viscosity of) the composition, resulting in a considerable reduction in molding time.

Hereafter, the present invention will be described in greater detail.

Crosslinking Agent (Component A)

The crosslinking agent, component A, reacts with the reactive functional group in the N-vinylcarboxamide copolymer (component B) contained in the liquid-absorbing material composition of the present invention.

Examples of the crosslinking agent include aldehydes such as formaldehyde, glyoxal, etc., N-methylol compounds such as N,N-dimethylolmelamine, etc., dicarboxylic acids such as fumaric acid, malonic acid, etc., epichlorohydrin, boric acid, amines such as ethylenediamine, etc., diols such as ethylene glycol, etc., bisepoxides such as ethylene glycol diglycidyl ether, etc., and diisocyanates such as ethylene diisocyanate, etc. However, the present invention is not limited thereto.

These crosslinking agents are selected according to the kind of the functional group contained in the N-vinylcarboxamide copolymer and are added in amounts sufficient for the crosslinked molded product of liquid-absorbing material to retain its shape upon absorbing liquids, more specifically within the range of proportion of component A: component B=0.001 to 90% by weight: 10 to 99.99% by weight. With the amount of less than 0.001% by weight, crosslinking is insufficient and noncrosslinked polymers are formed, so that the gel after absorption of liquids has insufficient strength and shape-retaining properties, thus failing to function as a liquid-absorbing agent. With the amount of above 90% by weight, various problems tend to arise, i.e. the density of crosslinking is so high that absorption magnification decreases and the portion of component A which does not participate in crosslinking reaction increases to a considerable extent to bleed out of the final molded product.

N-Vinylcarboxamide Based Copolymer (Component B)

The component B is a copolymer of N-vinylcarboxamide having a functional group which reacts with the component A, represented by general formula (IA):

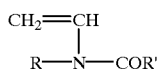

wherein R and represents a hydrogen atom or an alkyl group having 1 to 4 carbon atom(s) and R' represents an alkyl group having 1 to 4 carbon atom(s).

In general formula (IA) above, the alkyl groups represented by R and R' may be straight chain or branched.

Specific examples of the N-vinylcarboxamide represented by general formula (IA) include N-vinylformamide, N-vinylacetamide, N-vinylpropionamide, N-vinylbutanamide, N-vinylpentanamide, N-vinyl-N-methylformamide, N-vinyl-N-methylacetamide, N-vinyl-N-methylpropaionamide, N-vinyl-N-methylbutanamide, N-vinyl-N-methylpentanamide, N-vinyl-N-ethylformamide, N-vinyl-N-ethylacetamide, N-vinyl-N-ethylpropionamide, N-vinyl-N-ethylbutanamide, N-vinyl-N-ethyl-pentanamide, N-vinyl-N-propylformamide, N-vinyl-N-propylacetamide, N-vinyl-N-propylpropionamide, N-vinyl-N-propylbutanamide, N-vinyl-N-propylpentanamide, N-vinyl-N-butylformamide, N-vinyl-N-butylacetamide, N-vinyl-N-butylpropionamide, N-vinyl-N-butylbutanamide, and N-vinyl-N-butyl-pentanamide. Among these, N-vinyl-N-methylacetamide and N-vinylacetamide are preferred. The particularly preferred is N-vinylacetamide.

The component B is added in amounts within the range of 10 to 99.99% by weight based on the total weight of the component A and the component B. With the content of less than 10% by weight, the molded product has insufficient liquid absorbency since the proportion of the N-vinylcarboxamide copolymer is too small. On the other hand, when the content of the component B exceeds 99.99% by weight, the viscosity of the liquid-absorbing material composition increases too much so that the liquid-absorbing material composition tends to be difficult to mold.

Examples of the functional group which reacts with the crosslinking agent (component A) and has a strong affinity for water include a hydroxyl group, a hydroxyalkyl group, a carboxyl group, a sulfonic acid group, a phosphoric acid group an aminocarbonyl group, a mono- or di-lower alkyl-aminocarbonyl group, an amino group, a mono- or di-lower alkyl-amino group, an ether group, an amide group, an ester group, a pyrrolidone group, a lactide group, an imide group, a phosphoric ester group, a quaternary ammonium group, a cyano group, a thiol group, an epoxy group, a urethane group, a nitro group, a sulfide group, etc. However, the present invention is limited thereto.

The copolymer of N-vinylcarboxamide is preferably one which substantially comprises a repeating unit represented by general formula (I):

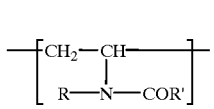

wherein R and represents a hydrogen atom or an alkyl group having 1 to 4 carbon atom(s) and R' represents an alkyl group having 1 to 4 carbon atom(s); general formula (II):

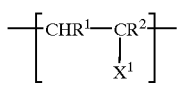
(II)

wherein $R^1$ represents a hydrogen atom or a carboxyl group or its alkali salts, $R^2$ represents a hydrogen atom, a methyl group or a carboxyl group or its alkali salts, $X^1$ represents a carboxyl group or its alkali salts provided, or $R^1$ and $X^1$ taken together with the carbon atoms to which they are attached form a cyclic acid anhydride structure; general formula (III):

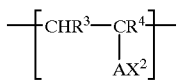
(III)

wherein $R^3$ and $R^4$ independently represent a hydrogen atom, a $C_1$~$C_4$-alkyl group or a carboxyl group or its alkali salts, A is a group represented by general formula (V), (VI) or (VII):

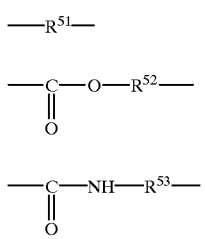
(V)
(VI)
(VII)

wherein $R^{51}$, $R^{52}$ and $R^{53}$ independently represent a $C_1$~$C_{10}$-straight chain or branched alkylene group, $X^2$ represents a carboxyl group, a phosphoric group or their alkali salts, or $R^3$ and $X^2$ taken together with the carbon atoms to which they are attached form a cyclic acid anhydride structure; and/or general formula (IV):

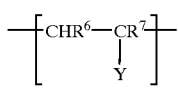
(IV)

wherein $R^6$ and $R^7$ independently represent a hydrogen atom or a $C_1$~$C_4$-alkyl group, Y represents a $C_1$~$C_4$-hydroxyalkyl group, —$CH_2NR^8R^9$ ($R^8$ and $R^9$ independently represent a hydrogen atom, a $C_1$~$C_4$-alkyl group or a $C_1$~$C_4$-alkenyl group), —$COOR^{10}$ ($R^{10}$ represents a $C_1$~$C_4$-alkyl group or a $C_1$~$C_4$-hydroxyalkyl group), —$CONR^{11}R^{12}$ ($R^{11}$ and $R^{12}$ independently represent a hydrogen atom, a $C_1$~$C_4$-alkyl group, a $C_3$~$C_5$-alkenyl group or a methylol group), —$CONH$—$R^{13}$—$NR^{14}R^{15}$ ($R^{13}$ represents a simple chemical bond or the same group as defined by A above, and $R^{14}$ and $R^{15}$ independently represent the same groups as $R^{11}$ and $R^{12}$ above), or their quaternary ammonium salts, or a phenyl group substituted with 1 to 3 hydroxyl groups at the nucleus thereof, with the repeating unit (I) occupying 99.99 to 50% by weight, repeating units (II), (III) and/or (IV) occupying 0.01 to 50% by weight.

In the definition of repeating unit above, by the term "substantially" is meant that those compositions containing repeating units derived from polymeric by-products and the like that cannot be removed during the process of preparing the starting monomers may fall within the above definition.

When the concentration of ethylenically unsaturated monomers contained in the N-vinylcarboxamide copolymer is less than 0.01% by weight, crosslinking does not proceed sufficiently in the liquid-absorbing material composition, so that the liquid-absorbing molded product obtained from the liquid-absorbing material composition of this invention becomes a non-uniform gel when the molded product absorbs liquids due to liberation of separation liquid and unreacted polymers. In case where the amount of the ethylenically unsaturated monomers exceeds 50% by weight, the affinity of the solvent is decreased, making it impossible to blend a large amount of solvents so that the viscosity of the liquid-absorbing material to be obtained increases, resulting in failure of molding it.

The N-vinylcarboxamide copolymer, component B, is specifically a random copolymer comprising a repeating unit represented by one of general formulae (VIII) to (X):

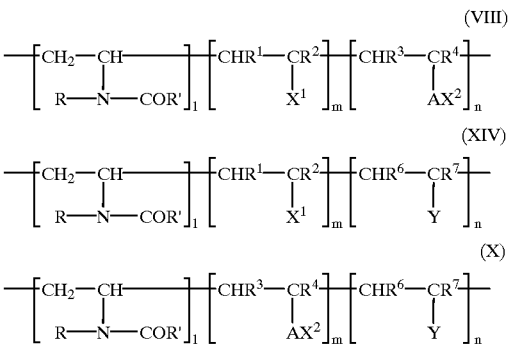
(VIII)
(XIV)
(X)

In the above formulae, the symbols have the same meanings as described above, and l=50 to 99.99% by weight, m=0.01 to 50% by weight, and n=0.01 to 50% by weight provided that m+n=0.01 to 50% by weight.

In the repeating units (VIII) to (X), the structural unit represented by general formula (II)

(II)

can be introduced by copolymerizing the following monomers. More particularly, the monomers include acrylic acid, methacrylic acid, crotonic acid, maleic acid, fumaric acid, citraconic acid, cinnamic acid, and salts thereof when $X^1$ is a carboxyl group or its alkali salts, whereas maleic anhydride when $R^1$ and $X^1$ independently are a carboxyl group or its alkali salts and formula (II) is a cyclic acid anhydride structure.

The structural unit represented by general formula (III)

(III)

can be introduced by copolymerizing the following monomers. More particularly, when A has a structure represented by general formula (V):

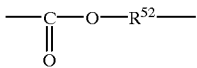
(V)

the monomers for $X^2$ being a carboxyl group or its alkali salts include, for example, itaconic acid, aconitic acid, 3-butenoic acid, 4-pentenoic acid, ω-undecenic acid and salts thereof.

When A has a structure represented by general formula (VI):

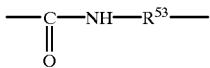
(VI)

the monomers for $X^2$ being a carboxyl group or its alkali salts include, for example, carboxyethyl acrylate and salts thereof; the monomers for $X^2$ being phosphoric acid or alkali salts thereof include, for example, 2-acryloylethylphosphoric acid, 3-acryloyl-propylphosphoric acid, 4-acryloylbutylphosphoric acid, 6-acryloylhexylphosphoric acid, 8-acryloyloctyl-phosphoric acid, 2-methacryloylethylphosphoric acid, 3-methacryloylpropylphosphoric acid, 4-methacryloyl-butylphosphoric acid, 6-methacryloylhexylphosphoric acid, 8-methacryloyloctylphosphoric acid, and salts thereof.

When A has a structure represented by general formula (VII):

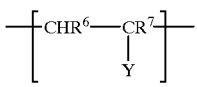
(VII)

the monomers for $X^2$ being a carboxyl group or alkali salts thereof include, for example, N-methallyl-α-amino acids and salts thereof.

Further, the structural unit represented by general formula (IV)

$$\left[ CHR^6 - \underset{Y}{CR^7} \right]$$ (IV)

can be introduced by copolymerizing the following monomers.

More particularly, when Y represents a $C_1 \sim C_4$-hydroxyalkyl group, the monomers include, for example, allyl alcohol, methallyl alcohol, crotyl alcohol, etc.;

when Y represents $CH_2NR^8R^9$, the monomers include, for example, monoallylamine, methallylamine, N,N-dimethyl-allylamine, N,N-diethyl-allylamine, dimethallylamine, N-ethyldiallylamine, N,N-dimehtyl-N,N-diallylamine, and quaternary ammonium salts thereof;

when Y represents $COOR^{10}$, the monomers include, for example, hydroxyethyl methacrylate, hydroxypropyl methacrylate, hydroxybutyl methacrylate, methyl crotonate, ethyl crotonate, t-butyl crotonate, etc.;

when Y represents $CONR^{11}R^{12}$, the monomers include, for example, acrylamide, methacrylamide, N-methyl-acrylamide, N-ethylacrylamide, N-n-propylacrylamide, N-i-propylacrylamide, N-n-butylacrylamide, N-i-butylacrylamide, N-t-butylacrylamide, N-methylol-acrylamide, N-allylacrylamide, N-methylmethacrylamide, N-ethylmethacrylamide, N-n-propylmethacrylamide, N-i-propylmethacrylamide, N-n-butylmethacrylamide, N-i-butylmethacrylamide, N-t-butylmethacrylamide, N-methylolmethacrylamide, N-allylmethacrylamide, N,N-dimethylacrylamide, N,N-diethylacrylamide, N,N-diisopropylacrylamide, N,N-di-n-butylacrylamide, etc.;

when Y represents $CONH-R^{13}-NR^{14}R^{15}$ or quaternary salts thereof, the monomers include, for example, N,N-dimethylaminoethylacrylamide, N,N-dimethylamino-ethylmethacrylamide, N,N-dimethylaminopropyl-acrylamide, N,N-dimethylaminopropylmethacrylamide, etc.; and when Y represents a phenyl group substituted with 1 to 3 hydroxyl group(s) at the nucleus, the monomers include, for example, styrene, o-(or m- or p-)methyl-styrene, 2,4-(or 2,5-, 2,6-, or 3,5-)dimethylstyrene, 2,4,5-(or 2,4,6-)trimethylstyrene, pentamethylstyrene, o-(or m- or p-)ethylstyrene, 2,4-(or 2,5-, 2,6-, or 3,5-)diethylstyrene, 2,4,5-(or 2,4,6-)triethylstyrene, 2,3,4,5-tetraethylstyrene, pentaethylstyrene, o-(or m- or p-)n-butylstyrene, o-(or m- or p-)allylstyrene, o- (or m- or p-)chlorostyrene, o- (or m- or p-)fluoro-styrene, 2,3-(or 2,4-, 2,5-, 2,6-, or 3,5-)dichloro-styrene, o-(or m- or p-)methoxy-styrene, 2,3-(or 2,4-, 2,5-, 2,6-, or 3,5-)dimethoxystyrene, 2,3,4-trimethoxystyrene, o-(or m- or p-)hydroxystyrene, 2,5-dihydroxystyrene, o-(or m- or p-)aminostyrene, o-(or m- or p-)N,N-dimethylaminostyrene, α-methylstyrene, α-ethyl-styrene, α-n-propylstyrene, β-methylstyrene, β-ethylstyrene, β-i-propylstyrene, β-n-butylstyrene, etc.

Hereinbelow are presented specific examples of the copolymers having the repeating units represented by general formulae (VIII) to (X), respectively. Here, by the term "partial or complete neutralization products" are meant those compounds in which a part or all of the hydrogen ions in the functional group such as carboxylic acid, sulfonic acid, phosphoric acid etc., in the copolymer is substituted with a cation such as alkali metals, sodium, potassium, etc. or alkaline earth metals, for example, calcium, barium, etc.

First, examples of the copolymer represented by general formula (VIII) include N-vinylcarboxamide/acrylic acid copolymer and its partial or complete neutralization products, N-vinylcarboxamide/methacrylic acid copolymer and its partial or complete neutralization products, N-vinylcarboxamide/crotonic acid copolymer and its partial or complete neutralization products, N-vinylcarboxamide/maleic acid copolymer and its partial or complete neutralization products, N-vinylcarboxamide/fumaric acid copolymer and its partial or complete neutralization products, N-vinylcarboxamide/citraconic acid copolymer and its partial or complete neutralization products, N-vinylcarboxamide/cinnamic acid copolymer and its partial or complete neutralization products, N-vinylcarboxamide/maleic anhydride copolymer and its partial or complete neutralization products, N-vinylcarboxamide/itaconic acid copolymer and its partial or complete neutralization products, N-vinylcarboxamide/aconitic acid copolymer and its partial or complete neutralization products, N-vinylcarboxamide/3-butenoic acid copolymer and its partial or complete neutralization products, N-vinylcarboxamide/4-pentenoic acid copolymer and its partial or complete neutralization products, N-vinylcarboxamide/carboxyethyl acrylate copolymer and its partial or complete neutralization products, N-vinylcarboxamide/acrylic acid/itaconic acid copolymer and its partial or complete neutralization products, N-vinylcarboxamide/methacrylic acid/aconitic acid copolymer and its partial or complete neutralization products, N-vinylcarboxamide/acrylic acid/3-butenoic acid copolymer and its partial or complete neutralization products, N-vinylcarboxamide/methacrylic acid/4-pentenoic acid copolymer and its partial or complete neutralization products, N-vinylcarboxamide/vinylsulfonic acid/itaconic acid copolymer and its partial or complete neutralization products, N-vinylcarboxamide/acrylic acid/allylsulfonic acid copolymer and its partial or complete neutralization products, N-vinylcarboxamide/maleic acid/allylphosphoric acid copolymer and its partial or complete neutralization products, N-vinylcarboxamide/fumaric acid/carboxyethyl acrylate copolymer and its partial or complete neutralization products, and the like.

Next, examples of the copolymer represented by general formula (IX) above include N-vinylcarboxamide/allyl alcohol copolymer and its partial or complete neutralization products, N-vinylcarboxamide/methallylamine copolymer and its partial or complete neutralization products, N-vinylcarboxamide/N,N-diethylallylamine copolymer and its partial or complete neutralization products, N-vinylcarboxamide/ethyl methacrylate copolymer and its partial or complete neutralization products, N-vinylcarboxamide/t-butyl acrylate copolymer and its partial or complete neutralization products, N-vinylcarboxamide/hydroxyethyl methacrylate copolymer and its partial or complete neutralization products, N-vinylcarboxamide/hydroxypropyl methacrylate copolymer and its partial or complete neutralization products, N-vinylcarboxamide/dimethylaminoethyl acrylate copolymer and its partial or complete neutralization products, N-vinylcarboxamide/diethylene glycol ethoxyacrylate copolymer and its partial or complete neutralization products, N-vinylcarboxamide/acrylamide copolymer and its partial or complete neutralization products, N-vinylcarboxamide/N-methylacrylamide copolymer and its partial or complete neutralization products, N-vinylcarboxamide/N-methylolacrylamide copolymer and its partial or complete neutralization products, N-vinylcarboxamide/N,N-diethylacrylamide copolymer and its partial or complete neutralization products, N-vinylcarboxamide/N,N-dimethylaminoethylacrylamide copolymer and its partial or complete neutralization products, N-vinylcarboxamide/N-vinyl-N,N-dimethylamine copolymer and its partial or complete neutralization products, N-vinylcarboxamide/p-hydroxystyrene copolymer and its partial or complete neutralization products, N-vinylcarboxamide/p-aminostyrene copolymer and its partial or complete neutralization products, N-vinylcarboxamide/acrylic acid/allyl alcohol copolymer and its partial or complete neutralization products, N-vinylcarboxamide/maleic acid/methallylamine copolymer and its partial or complete neutralization products, N-vinylcarboxamide/acrylic acid/N,N-dimethylallylamine copolymer and its partial or complete neutralization products, N-vinylcarboxamide/maleic acid/t-butyl methacrylic acid copolymer and its partial or complete neutralization products, N-vinylcarboxamide/acrylic acid/hydroxypropyl methacrylate copolymer and its partial or complete neutralization products, N-vinylcarboxamide/acrylic acid/acrylamide copolymer and its partial or complete neutralization products, N-vinylcarboxamide/acrylic acid/N-methylolacrylamide copolymer and its partial or complete neutralization products, N-vinylcarboxamide/methacrylic acid/N,N-diethylacrylamide copolymer and its partial or complete neutralization products, N-vinylcarboxamide/maleic acid/N,N-dimethylaminoethylmethacrylamide copolymer and its partial or complete neutralization products, N-vinylcarboxamide/fumaric acid/N-vinyl-N,N-dimethylamine copolymer and its partial or complete neutralization products, and the like.

Further, examples of the copolymer represented by general formula (X) include N-vinylcarboxamide/itaconic acid/allyl alcohol copolymer and its partial or complete neutralization products, N-vinylcarboxamide/aconitic acid/N,N-dimethylallylamine copolymer and its partial or complete neutralization products, N-vinylcarboxamide/itaconic acid/hydroxyethyl methacrylate copolymer and its partial or complete neutralization products, N-vinyl-carboxamide/3-butenoic acid/hydroxypropyl methacrylate copolymer and its partial or complete neutralization products, N-vinylcarboxamide/4-pentenoic acid/diethylaminoethyl methacrylate copolymer and its partial or complete neutralization products, N-vinylcarboxamide/itaconic acid/N-methylolacrylamide copolymer and its partial or complete neutralization products, N-vinylcarboxamide/2-acrylamide-2-methylpropanesulfonic acid/N,N-dimethylaminoethylmetahcrylamide copolymer and its partial or complete neutralization products, N-vinylcarboxamide/2-acrylamide-2-methylpropanesulfonic acid/N-vinylpropionamide copolymer and its partial or complete neutralization products, and the like.

In the liquid-absorbing material composition of the invention, there can be used monomers other than the N-vinylcarboxamide and ethylenically unsaturated monomers containing in the molecule one of the structures represented by general formulae (II) to (IV) in amounts within the range where the performance of the gel as a crosslinked molded product is not deteriorated. These monomers may be copolymerized in order to increase the tackiness or flexibility of the resulting molded product of liquid-absorbing material in amounts where the affinity of the copolymer for solvents is not damaged. Examples of such monomers include functional monomers such as methyl acrylate, methyl vinyl ether, methyl methacrylate, methoxyethyl acrylate, and acrylonitrile, vinyl monomers such as vinyl acetate, vinyl propionate and N-vinylpyrrolidone, and the like. However, this invention is not limited thereto.

Use of N-vinylcarboxamide copolymer can give rise to gels which exhibit excellent properties and absorb aqueous solutions containing electrolytes such as in high concentrations and alcohols and even when they contain water or alcohols already, which further absorb a large amount of water or alcohols upon contact with these liquids freshly. Since the nonionic copolymer is used as the major component, the gels are stable against pH and electrolytes.

For manufacturing the copolymers, various monomers can be copolymerized using a polymerization initiator in a conventional manner, for example, by an aqueous solution polymerization, precipitation polymerization, reverse phase suspension polymerization, or the like. After completion of the polymerization, viscous liquid, agar-like or powdery products can be obtained. After dehydration and drying, the viscous liquid and agar-like products can further be converted into powder, which is suitable for manufacturing the liquid-absorbing material composition of this invention.

Crosslinking Reaction

As the method for crosslinking the crosslinking agent (component A) and N-vinylcarboxamide (component B), there can be used a method which employs a crosslinking reaction with the reactive group in the component B such as a hydroxyl group, a hydroxyalkyl group, a carboxyl group, a sulfonic acid group, a phosphoric acid group, an aminocarbonyl group, a mono- or di-lower alkyl-aminocarbonyl group, an amino group, a mono- or di-lower alkyl-amino group, or the like.

Hereafter, the crosslinking reaction in the composition of this invention will be described. However, this invention is not limited thereto. Also, two or more crosslinking reactions may be used.

(1) Examples of the crosslinking reaction using a hydroxyl group or a hydroxyalkyl group include methods in which a copolymer containing, as the above-described structural unit represented by formula (IV), hydroxyethyl (meth)acrylate, hydroxypropyl (meth)acrylate, hydroxybutyl (meth)acrylate, N-methylolacrylamide, (meth)allyl alcohol, crotyl alcohol, hydroxymethyl vinyl ketone, o-(or m- or p)-hydroxystyrene, 2,5-dihydroxystyrene, or the like is reacted with (i) aldehydes such as formaldehyde, glyoxal, terephthalaldehyde, etc., for example formaldehyde, to obtain a random-crosslinked product having crosslinking sites represented by formula (XI):

$$-O-CH_2-O- \quad (XI)$$

(ii) N-methylol compounds such as N,N'-dimethylolurea, N,N'-dimethylolmelamine, N,N'-dimethylolethyleneurea, etc., for example, N,N'-dimethylolethyleneurea, to obtain a random-crosslinked product having crosslinking sites represented by formula (XII):

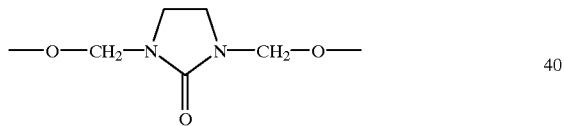

(XII)

(iii) dicarboxylic acids such as oxalic acid, malonic acid, succinic acid, tartaric acid, itaconic acid, fumaric acid, maleic acid, glutaric acid, adipic acid, etc., for example, fumaric acid, to obtain a random-crosslinked product having crosslinking sites represented by formula (XIII):

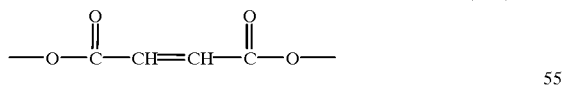

(XIII)

(iv) epichlorohydrin to obtain a random-crosslinked product having crosslinking sites represented by formula (XIV):

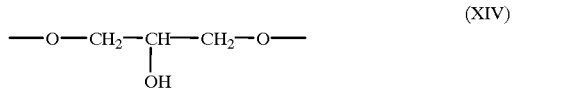

(XIV)

(v) boric acid to obtain a random-crosslinked product having crosslinking sites represented by formula (XV):

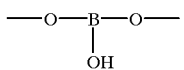

(XV)

(2) Examples of the crosslinking reaction using a carboxyl group include methods in which a copolymer containing, as the above-described structural unit represented by formula (II) or (III), (meth)acrylic acid, crotonic acid, fumaric acid, maleic acid, malonic acid, citraconic acid, itaconic acid, aconitic acid, vinyl acetate, allyl acetate, ω-undecenoic acid, carboxyethyl acrylate, N-methallyl-α-amino acid, cinnamic acid, or the like or salts thereof is reacted with (vi) diamines such as ethylenediamine, N-methylethylenediamine, N,N'-dimethylethylenediamine, N,N'-diethylethylenediamine, N,N'-dipropylethylenediamine, N,N'-dibutylethylenediamine, p-phenylenediamine, p,p'-diaminodiphenylmethane, etc., for example, ethylene diamine, to obtain a random-crosslinked product having crosslinking sites represented by formula (XVI):

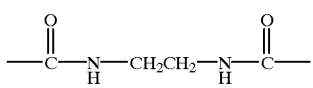

(XVI)

(vii) diols such as ethylene glycol, diethylene glycol, triethylene glycol, tetraethylene glycol, etc., for example, ethylene glycol, to obtain a random-crosslinked product having crosslinking sites represented by formula (XVII):

(XVII)

(viii) bisepoxides such as ethylene glycol diglycidyl ether, 1,1-bis(4-glycidyloxyphenyl)ethane, sorbitol polyglycidyl ether, sorbitan polyglycidyl ether, polyglycerol polyglydicyl ether, pentaerythritol polyglycidyl ether, diglycerol polyglycidyl ether, triglycidyl tris(2-hydroxyethyl)isocyanate, glycerol polyglycidyl ether, trimethylolpropane polyglycidyl ether, resorcin diglycidyl ether, neopentyl glycol diglycidyl ether, 1,6-hexanediol diglycidyl ether, polyethylene glycol diglycidyl ether, propylene glycol diglycidyl ether, polypropylene glycol diglycidyl ether, polytetramethylene glycol diglycidyl ether, allyl glycidyl ether, 2-ethylhexyl glycidyl ether, phenyl glycidyl ether, phenyl $(EO)_5$ glycidyl ether, p-tert-butylphenyl glycidyl ether, lauryl alcohol $(EO)_{15}$ glycidyl ether, adipic acid diglycidyl ether, o-phthalic acid diglycidyl ether, hydroquinone diglycidyl ether, bisphenol S diglycidyl ether, terephthalic acid diglycidyl ether, glycidylphthalimide, dibromophenyl glycidyl ether, dibromopentyl glycol diglycidyl ether, diglycidyl terephthalate, etc., for example, ethylene glycol diglycidyl ether to obtain a random-crosslinked product having crosslinking sites represented by formula (XVIII):

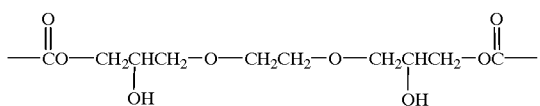

(XVIII)

(ix) diisocyanates such as methylene diisocyanate, ethylene diisocyanate, trimethylene diisocyanate, 1-methylethylene diisocyanate, tetramethylene diisocyanate, p-phenylene diisocyanate, p,p'-diphenylmethane diisocyanate, etc., for example, methylene diisocyanate, to obtain a random-crosslinked product having crosslinking sites represented by formula (XIX):

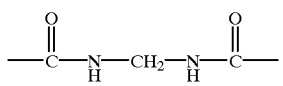

(XIX)

and the like methods.

Crosslinking Reaction Controlling Agent

Further, there can be used as a crosslinking reaction rate controlling agent organic acids, organic acid salts, organic bases such as citric acid lactic acid, glycolic acid, malic acid, fumaric acid, methanesulfonic acid, maleic acid, acetic acid, EDTA-disodium, urea, triethylamine, ammonia, etc. as well as inorganic acids such as hydrochloric acid, phosphoric acid, sulfuric acid, nitric acid, hydrobromic acid, and the like. Particularly, when the crosslinking agent is an epoxy compound, there can be used various curing catalysts such as quaternary ammonium salts, e.g., triethylbenzylammonium chloride, tetramethylammonium chloride, etc., tertiary amines, e.g., benzylmethylamine, tributylamine, tris(dimethylamino) methylphenols, etc., imidazole compounds, e.g., 2-methyl-4-ethylimidazole, 2-methylimidazole, etc., as well as $SnCl_2$, $Zn(BF_4)_2$, etc.

Water (Component C)

Water, component C, is added in order to promote the crosslinking reaction. The amount of water to be added is 10 to 65% by weight based on the total weight of the composition. When the amount is less than 10% by weight, the crosslinking reaction is too slow while use of the amount of greater than 65% by weight increases considerably the time required for drying after molding.

Water-Soluble Oraanic Solvent (Component D)

Water-soluble organic solvent, component D, is added in order to allow the liquid-absorbing composition (sol) to form a layer having a strength sufficient for the layer to be molded continuously. It may be added in any desired amount within the range of 10 to 90% by weight based on the total weight of the composition. With the amount of less than 10% by weight, a large amount of water has to be added before the sol can have a viscosity sufficient for the sol to be molded into a desired shape, in which case it takes a long time for drying and molding the sol. On the other hand, when the water-soluble organic solvent is used in excess amounts, i.e., in amounts exceeding 90% by weight, the hydrophilic polymer in the component B becomes difficult to dissolve so that it is difficult to mold the resulting composition. Note that the component D also can serve as a plasticizer.

The water-soluble organic solvent used in this invention may be any solvent, as long as the smallest part of the solvent can dissolve in water, and examples thereof include lower monohydric alcohols such as methanol, ethanol, and propanol, acetone, methyl ethyl ketone, cyclohexanone, cellosolve, dioxane, dimethylformamide (DMF), butyl acetate, dimethyl sulfoxide (DMSO), tetrahydrofuran (THF), acetonitrile, N-methylpyrrolidone, glycols, ethyl acetate, and the like.

Plasticizer (Component E)

Plasticizer (component E) is added in order to give flexibility to the films and the like after the molding. The amount of the plasticizer to be added is 1/10 to 10/1 in a weight proportion of component B to the plasticizer. Where no plasticizer is added, the resulting molded product is brittle.

Those plasticizers that do not give adverse effects on the characteristics of the liquid-absorbing resin composition are selected for use. The plasticizer is preferably polyhydric alcohol. Examples of the polyhydric alcohol include ethylene glycol, propylene glycol, 1,3-butylene glycol, 2,3-butylene glycol, ethylene glycol monobutyl ether, glycerin, diethylene glycol, triethylene glycol, 1,4-butylene glycol (dihydric alcohol), glycerol, trioxyisobutane (trihydric alcohol), erythritol, pentaerythritol (tertahydric alcohol), xylitol, adnitol (pentahydric alcohol), allodulcitol, sorbitol (hexahydric alcohol), etc.

Hydrophilic Polymer Which Does Not Crosslink With Component A (Component F)

The liquid-adsorbing material of this invention may contain other hydrophilic polymer that has no functional group capable of crosslinking with the component A (component F) in order to improve its moldability or shape retention of the gel. Examples of the hydrophilic polymer include natural polymers such as gum Arabic, tragacanth gum, locust bean gum, guar gum, echo gum, karaya gum, agar, starch, carrageenan, alginic acid, alginates (for example, sodium alginate), propylene glycol alginate, dextran, dextrin, amylose, gelatin, collagen, pullulan, pectin, amylopectin, sodium amylopectin semiglycolate, chitin, albumin, casein, polyglutamic acid, and polyaspartic acid; semi-synthetic polymers such as methylcellulose, ethylcellulose, propylcellulose, ethylmethylcellulose, hydroxycellulose, hydroxyalkylcellulose, hydroxypropylmethylcellulose, hydroxypropyl starch, carboxymethyl starch, alkali metal carboxymethylcellulose, alkali metal cellulose sulfate, cellulose graft polymer, crosslinked gelatin, cellulose acetate terephthalate, starch-acrylic acid graft copolymer, phthalic anhydride-modified gelatin, and succinic acid-modified gelatin; synthetic polymers such as polyvinylpyrrolidone, polyvinyl methyl ether, polymethyl vinyl ester, carboxyvinyl polymer, vinylpyrrolidone/ethyl acrylate copolymer, vinylpyrrolidone/styrene copolymer, vinylpyrrolidone/vinyl acetate copolymer, N-vinylacetamide homopolymer, vinyl acetate/crotonic acid copolymer, polyvinylsulfonic acid, N-vinylacetamide crosslinked product, polyacrylamide, etc. However, this invention is not limited thereto. In other words, the component F can be selected appropriately from the hydrophilic polymers that do not crosslink with the component A, taking into consideration the reactivity with the component A.

Tackifying Substance

The liquid-absorbing material of this invention may contain a tackifying substance. Examples of the tackifying substance include rubber based tackifying substances such as silicone gum, polyisoprene rubber, styrene block copolymer rubber, acrylic rubber, and natural rubber, vinyl based tackifying substances such as polyvinyl alkyl ether, polyvinyl alcohol, and polyvinyl acetate, cellulose based tackifying substances such as carboxymethyl cellulose, (meth) acrylate based tackifying substances containing as the major component alkyl (meth)acrylate, and the like. However, this invention is not limited thereto.

Other Additives

In order to allow it to well exhibit its characteristics, improve its processability and moldability, improve the quality of the product therefrom, enhance the dispensability and stability of the agents in the molded liquid-absorbing material, or for some other purposes, the liquid-absorbing material of this invention may optionally contain one or more additives selected from powder materials, oily raw materials, acids, alkalis, humectants, astringents, anti-itching agents, cornea softening agents, surfactants, coloring agents, perfumes, ultraviolet light screening agents, antiseptics and microbicides, antioxidants, and the like in any desired amounts as far as the performance of the molded liquid-absorbing material is not deteriorated.

The powder raw materials may include montmorillonite, silicic anhydride, gypsum, carbon black, diatomaceous earth, red oxide, calcium carbonate, hydrotalcite, talc, glass, kaolin, bentonite, metal soap, aerosil, titanated mica, bismuth oxychloride, fish scale guanine, zinc white, titanium dioxide, and the like.

The oily raw materials include almond oil, olive oil, hardened oil, camellia oil, castor oil, Japan wax oil, coconut oil, beeswax, spermaceti, lanolin, carnauba wax, candelilla wax, liquid paraffin, vaseline, paraffin, microcrystalline wax, ceresin, squallene, lauric acid, myristic acid, palmitic acid, stearic acid, isostearic acid, oleic acid, lauryl alcohol, cetanol, stearyl alcohol, oleyl alcohol, octyldodecanol, cholesterol, hexyldecanol, white sterol, cetyl lactate, isopropyl myristate, hexyl laurate, myristyl myristate, isopropyl palmitate, octyldodecanol myristate, butyl stearate and the like.

The acids include citric acid, tartaric acid, lactic acid, glycolic acid, hydrochloric acid, nitric acid, malic acid, phosphoric acid, and the like.

The alkalis include sodium hydroxide, potassium hydroxide, ammonia water, triethanolamine, diethanolamine, monoethanolamine, borax methyldiethanolamine, diisopropanolamine, polyethanolamine, and the like.

The humectants include glycerol, propylene glycol, sorbitol, 1,3-butylene glycol dl-pyrrolidonecarboxylic acid, sodium lactate, and the like.

The astringents include citric acid, tartaric acid, lactic acid, aluminum chloride, aluminum sulfate, allantoin chlorohydroxyaluminum, allantoin dihydroxyaluminum, aluminum phenolsulfate, zinc paraphenolsulfonate, zinc sulfate, aluminum chlorohydroxide, and the like.

The anti-itching agents include camphor, thymol, menthol, polyoxyethylene lauryl ether, antihistaminics, ethyl aminobenzoate, and the like.

The cornea softening agents include sulfur, thioxolone, selenium sulfide, salicylic acid, resorcin, and the like.

The surfactants include anionic surfactants such as lauryl sulfates, polyoxyethylene alkyl ether sulfates, alkylbenzenesulfonates, polyoxyethylene alkyl ether phosphoric acid, polyoxyethylene alkyl phenyl ether phosphoric acid, and N-acylamino acid; cationic surfactants such as benzalkonium chloride, benzetonium chloride, stearyltrimethylammonium chloride, distearyldimethylammonium chloride, and stearyldimethylbenzylammonium chloride; amphoteric surfactants such as alkyldiaminoethylglycine hydrochloride, 2-alkyl-N-carboxymethyl-N-hydroxyethylimidazolinium betaine, and lauryl dimethylaminoacetic acid betaine; nonionic surfactants such as polyol fatty acid esters, glycerol monostearate, lipophilic type glycerol monooleate, ethylene glycol monostearate, propylene glycol monostearate, sorbitan fatty acid ester, polyoxyethylene sorbitan fatty acid ester, polyoxyethylene fatty acid ester, polyoxyethylene alkyl ether, polyoxyethylene alkyl phenol ether, polyoxyethylene sorbitol fatty acid ester, N-acylamino acid ester, sucrose fatty acid ester, and fatty acid alkylolamide; and the like.

The coloring agents include yellow oxide of iron, red oxide of iron, black oxide of iron, ultramarine, carbon black, hydrated chromium oxide, chromium oxide, tar pigments, lakes, and the like.

The perfumes include vegetable perfumes such as mustard oil, orange oil, sesame oil, jasmine oil, Japan cedar oil, iris oil, turpentine oil, orange flower oil, rose oil, eucalyptus oil, lime oil, lemon oil, Japanese mint oil, and rosemary oil, animal perfumes such as musk, civet, castoreum, and ambergris, hydrocarbon-based perfumes such as bromostyrol, pinene, and limonene, alcohol-based perfumes such as benzyl alcohol, and 1-menthol, ester-based perfumes such as ethyl acetate and methyl salicylate, aldehyde-based perfumes such as benzaldehyde and salicylaldehyde, ketone-based perfumes such as camphor, muscone, musk ketone, and 1-menthone, ether-based perfumes such as safrol, phenol-based perfumes such as thymol, lactone-based perfumes, acid-based perfumes such as phenyl acetate, nitrogen compound-based perfumes such as indole, and the like.

The ultraviolet light screening agents include benzophenone-based ones such as ASL-24, Cyasorb UV-9, and Uvinul M-40, benzoic acid-based ones such as Salol, azole-based ones such as Tinuvin P, nitrile-based ones such as Uvinul N-35, urea-based ones such as Ancour UA, and the like.

Antiseptics and microbicides include acids such as benzoic acid, salicylic acid, dehydroacetate, sorbic acid, and boric acid, phenols such as phenol, chlorocresol, chloroxylenol, isopropylmethylphenol, resorcinol, o-phenylphenol, p-oxybenzoates, phenoxyethanol, thymol, hinokithiol, and thioxolone, halogenated bisphenols such as hexachlorophene and 2,4,4'-trichloro-2'-hydroxydiphenyl ether, amidated compounds such as trichlorocarbanilide, halocarbane, and undecylenoylmonoethanolamide, quaternary ammonium compounds such as benzalkonium chloride, alkylisoquinolinium bromide, benzetonium chloride, and cetylpyridinium chloride, amphoteric surfactants such as lauryl di(aminoethyl)glycine, zinc 2-pyridinethiol-1-oxide chloride, gluconic acid, chlorohexydine, thiram, N-trichloromethylthio-4-cyclohexene-1,2-dicarboximide, chlorobutanol, and the like.

The antioxidants include, nordihydroguaiaretic acid, guaiac resin, propyl pyrogallate, butyl hydroxyanisole, dibutylhydroxytoluene (BHT), tocopherol (vitamin E), and the like.

The composition of this invention may be blended with one or more of drugs, stabilizing agents, fillers, usability improving agents, preservatives, plasticizers, anti-aging agents, softening agents, pH controlling agents, deterioration preventing agents, and the like. These additives may be added in any desired amounts as far as they do not adversely affect the characteristics of the resulting liquid-absorbing material.

Manufacturing Method for Molded Liquid-Absorbing Material

The molded liquid-absorbing material of this invention can be manufactured by slowly adding a mixed solution containing water-soluble organic solvent (component D) and N-vinylcarboxamide copolymer (component B) to a solution of a crosslinking agent (component A) and a plasticizer (component E) in water (component C), dissolving and kneading the resulting mixture until a solution or sol of the composition having a viscosity suitable for molding can be obtained. The solution or sol of the composition is molded into a desired shape suitable for the purpose, such as film or sheet, and then the crosslinking reaction is promoted while evaporating the water or water-soluble organic solvent with heating if necessary. In this case, the water or water-soluble organic solvent may remain inside the final molded liquid-absorbing material. While the crosslinking reaction proceeds in several hours, the reaction time can be reduced by heat treatment.

The liquid-absorbing material can be molded in a manner similar to the molding of solutions of conventional thermoplastic resin composition.

For example, in order to make a liquid-absorbing film from the liquid-absorbing material composition of this invention, first a coat of the above-described sol is given on a releasing body by using an applicator or roller type coating machine. Then, after drying or heating it to evaporate the water or water-soluble organic solvent, the releasing body is released to obtain a liquid-absorbing film. For carrying the film on a support to form a sheet, a support may be coated or impregnated on one or both surfaces thereof with a suitable amount of the liquid-absorbing material, followed by drying. The support may be, for example, a molded article such as a laminated film, sheet or tape, which is made from paper, wood, metal, glass fibers, cloths (flannel, woven fabric, nonwoven fabric, etc.), synthetic resins (polyurethane, ethylene/vinyl acetate copolymer, polyvinyl chloride, polyester (e.g., polyethylene terephthalate), polyolefin (e.g., polyethylene, polypropylene, etc.) polyamide (e.g., nylon-6, nylon-66, etc.), polyvinylidene chloride, polytetrafluoroethylene, etc.), foils of metals such as aluminum, rubber or cellulose derivatives and a plastic film.

In order to shorten the drying time, it is desirable to conduct heat treatment. The temperature for heat treatment is not particularly limited but usually it is selected from the range of 20° C. to 250° C., preferably 40° C. to 180° C. The heating time varies depending on the heating temperature but generally lasts for 5 seconds to 48 hours, preferably 60 seconds to 24 hours. There can be used any desired heating method, for example, a method using a hot roll, a method using hot air, a method using infrared rays, and the like. For increasing the storage stability of the resulting film, sheet or the like, it is desirable to affix a releasing sheet treated with silicone or by any other suitable means to the surface coated with the liquid-absorbing material, or to treat the surface which is not coated with liquid-absorbing material with silicone or by any other suitable means so as to form a releasing surface, and to roll it over or superimpose it on the surface coated with an adhesive. As the releasing sheet, there can be used polyethylene film, polypropylene film, releasing paper, cellophane, polyvinyl chloride, polyester, and the like.

In order to use the molded liquid-absorbing material composition as a medium for administration of drugs, the active ingredient can be added to the composition in the step of kneading it or by letting the composition after drying absorb a solvent containing the chemical in such a manner as to comply with the initial purpose as to administration site and release rate.

The drugs may be used in combination of two or more kinds where necessary.

ADVANTAGEOUS EFFECT OF THE INVENTION

The liquid-absorbing material composition of this invention, which has a high flowability and gives a uniform continuous layer, is easy to mold and is suitable for directly preparing a film- or sheet-shaped molded product without secondary processing after converting it into powder as in the case of the conventional water-absorbing polymer gel. Further, the composition of this invention is of a simple composition and can be produced safely and at low costs.

With the liquid-absorbing material composition of this invention, there can be manufactured a molded product having an excellent liquid absorbency in short time by molding and crosslinking the composition.

The molded liquid-absorbing material obtained from the liquid-absorbing material composition of this invention has the following features:

(1) Solution Retaining Ability

The molded material of this invention does not release the liquid if compressed after the absorption of the liquid. The surface could only feel slightly damp but never makes hands wet.

(2) Self-Supporting Property

In the state where the molded material of this invention has absorbed a liquid, the liquid contained inside the material does not flow, and the material has a strong elasticity and will not be collapsed readily even when pushed.

(3) Thermal Stability

When sealed in a bag made of aluminum foil in the state of absorbing the liquid and left to stand in an incubator at 50° C. for 14 days, the molded material of this invention well maintained its original shape and no liquid released from within the gel.

(4) Transparency

The molded material of this invention is highly transparent and uniform in quality.

(5) Drug Retention

The molded material of this invention is excellent in its retention of drugs, perfumes and the like.

Because of having the above-described properties, the liquid-absorbing material of this invention can be utilized in various applications as described below.

(1) Foodstuff: for example, freshness retaining agent, moisture conditioning agent, and the like.

(2) Agriculture and horticulture: for example, seedling growing, soil improving agent, sheet for microbe cultivation, and the like.

(3) Construction: for example, anti-dewing agent, moisture conditioning agent, and the like.

(4) Sanitary: for example, paper diaper, sanitary goods, and the like.

(5) Civil engineering: for example, waste liquid solidification, aging, water sealing sheet, and the like.

(6) Industry: for example, water sealing material for optical fiber cables, dehydration of solvents, and the like.

(7) Drugs: for example, plasters such as formulation for percutaneous absorption, formulation for permucous absorption, and the like.

(8) Medical tools: for example, coolant for the affected part when temperature rises, therapeutical agent for cuts, therapeutical pads, gauge, therapeutical agent for burns, surgical pads, and the like.

(9) Cosmetics, extra-medical goods: for example, packs, suntanning goods, pimple goods, and the like.

(10) Daily necessaries: for example, diapers, towels, fragrants, adhesives, humectants, surface protecting agents, anti-dewing agents, freshness retaining agents, coolants, desiccants, and the like. However, this invention is not limited thereto.

BEST MODE FOR CARRYING OUT THE INVENTION

Next, usefulness of this invention will be described by examples. However, this invention should not be construed as being limited thereto. In the following description, "parts" means "parts by weight."

Hydrophilic Polymer

The hydrophilic polymers used in the examples are as follows. The proportions of the hydrophilic polymer component are by weight.
(1):N-Vinylacetamide/sodium acrylate=9/1
(2):N-Vinylacetamide/sodium acrylate/methoxyethyl acrylate=7/1/2
(3):Acrylamide/N-vinylacetamide/sodium acrylate=0.5/9/0.5.
(4):Acrylic acid/N-vinylacetamide=4.5/5.5
(5):N-Vinylacetamide/hydroxyethyl methacrylate=8/2
(6):N-Vinylacetamide/sodium acrylate=6/4
(7):Potassium acrylate/N-Vinylacetamide=3/7
(8):Polyacrylic acid (average molecular weight: 4,000,000
(9):Acrylamide/sodium acrylate=8/2
(10):Acrylic acid/sodium acrylate=5/5
(11):Polyvinyl alcohol The hydrophilic polymer (1) above (N-Vinylacetamide/sodium acrylate=9/1 (weight ratio)) was prepared as described below.

A 1-liter 3-necked separable flask was equipped with a thermometer and a nitrogen introducing pipe, and an aqueous solution of 225 g of N-vinylacetamide and 25 g of sodium acrylate in 740 g of deionized water was charged into the flask. After introduction of nitrogen gas to purge the dissolved oxygen, the liquid temperature was adjusted to 30° C., and 10 g of an aqueous 1% solution of 2,2'-azobis-2-aminodipropane dihydrochloride was added as a polymerization initiator, and polymerization was continued for 7 hours in a adiabatic state. The polymer mass thus obtained was cut into small pieces, which were put in acetone solution to dehydrate them, filtered and dried under vacuum, followed by pulverization to obtain a dry polymer.

As the other hydrophilic polymers (2) to (11) were used those prepared in the same manner as in the above-described method or those commercially available.

EXAMPLE 1

Liquid-Absorbing Material Composition (A)

The hydrophilic polymer (1) was dispersed in a mixed solution of ethanol and ethylene glycol in the proportion described below and the dispersion was kneaded in a kneader for 30 minutes while adding a mixed solution of ethylene glycol diglycidyl ether and purified water to obtain a liquid-absorbing material (A).

| Formulation | |
|---|---|
| Hydrophilic polymer (1) | 5 parts |
| Ethylene glycol | 5 parts |
| Ethylene glycol diglycidyl ether | 0.25 parts |
| Purified water | 20 parts |
| Ethanol | 69.75 parts |

EXAMPLE 2

Liquid-Absorbing Material Composition (B)

To a mixed solution of the hydrophilic polymer (2), purified water, and sorbitol polyglycidyl ether was slowly added a dispersion of titanium dioxide, methanol and polyethylene oxide in the proportion described below with kneading t obtain a liquid-absorbing material (B).

| Formulation | |
|---|---|
| Hydrophilic polymer (2) | 25 parts |
| Purified water | 44 parts |
| Titanium dioxide | 0.75 parts |
| Sorbitol polyglycidyl ether | 0.25 parts |
| Polyethylene oxide | 15 parts |
| Methanol | 15 parts |

EXAMPLE 3

Liquid-Absorbing Material Composition (C)

To a mixed solution of 2-methylimidazole, a crosslinked product between N-vinylacetamide and pentaerythritol (200/1 weight ratio), EPICROSS WS-500, and purified water was slowly added a dispersion of the hydrophilic polymer (3), ethanol and propylene glycol in the proportion described below with kneading to obtain a liquid-absorbing material (C).

| Formulation | |
|---|---|
| Hydrophilic polymer (3) | 4 parts |
| Propylene glycol | 4.55 parts |
| Purified water | 10 parts |
| Oxazoline based crosslinking agent (EPICROSS WS-500) | 0.5 parts |
| 2-Methylimidazole | 0.05 parts |
| Ethanol | 80 parts |
| Crosslinked product between N-vinylacetamide and pentaerythritol (200:1 by weight) | 1 parts |

EXAMPLE 4

Liquid-Absorbing Material Composition (D)

To a mixed solution of tris(dimethylamino)methylphenol, TAKENATE WB-700 and purified water was slowly added a dispersion of the hydrophilic polymer (4), isopropyl alcohol, acetone, propylene glycol and diethylene glycol in the proportion described below with kneading to obtain a liquid-absorbing material (D).

| Formulation | |
|---|---|
| Hydrophilic polymer (4) | 5 parts |
| Propylene glycol | 2 parts |
| Diethylene glycol | 29.95 parts |
| Purified water | 20 parts |
| Blocked isocyanate crosslinking agent (TAKENATE WB-700) | 20 parts |
| Isopropyl alcohol | 20 parts |
| Acetone | 3 parts |
| Tris(dimethylamino)methylphenol | 0.05 parts |

EXAMPLE 5

Liquid-Absorbing Material Composition (E)

To a mixed solution of 1,3-butanediol, glyoxal and purified water was slowly added a dispersion of the hydrophilic polymer (5), ethanol, and ethyl acetate in the proportion described below with kneading to obtain a liquid-absorbing material (E).

| Formulation | |
|---|---|
| Hydrophilic polymer (5) | 5 parts |
| 1,3-Butanediol | 5 parts |
| Purified water | 58 parts |
| glyoxal | 1.5 parts |
| Ethyl acetate | 0.5 parts |
| Ethanol | 30 parts |

EXAMPLE 6

Liquid-Absorbing Material Composition (F)

To a mixed solution of dipropylene glycol, xylitol, N,N'-dimethylolethyleneurea and purified water was slowly added a dispersion of the hydrophilic polymer (6), methanol, and DMSO in the proportion described below with kneading to obtain a liquid-absorbing material (F).

| Formulation | |
|---|---|
| Hydrophilic polymer (6) | 5 parts |
| N,N'-Dimethylolethyleneurea | 0.5 parts |
| Purified water | 30 parts |
| Methanol | 55 parts |
| DMSO | 2.5 parts |
| Dipropylene glycol | 5 parts |
| Xylitol | 2 parts |

EXAMPLE 7

Liquid-Absorbing Material Composition (G)

To a mixed solution of fumaric acid, polyethylene glycol #200, sorbitol and purified water was slowly added a dispersion of the hydrophilic polymer (7), ethanol and acetonitrile in the proportion described below with kneading to obtain a liquid-absorbing material (G).

| Formulation | |
|---|---|
| Hydrophilic polymer (7) | 15 parts |
| Polyethylene glycol #200 | 10 parts |
| Sorbitol | 10 parts |
| Purified water | 40 parts |
| Fumaric acid | 0.5 parts |
| Ethanol | 30 parts |
| Acetonitrile | 4.5 parts |

EXAMPLE 8

The liquid-absorbing material composition (A) prepared in Example 1 was coated on a releasing body made of polypropylene with a clearance of 0.5 mm using an applicator. After leaving it to stand at room temperature for 2 hours, it was heated at 50° C. for 1 hour to obtain a film-shaped molded liquid-absorbing material (a). The molded product was flexible and would not be torn with ease when it was drawn. Indicated below are liquid absorption magnifications obtained when the molded product was allowed to absorb water, brine and methanol, respectively.

| Magnification | |
|---|---|
| Water | 62.2 |
| Brine | 44.2 |
| Ethanol | 18.6 |

The gel formed after the molded product of this example absorbed the liquid did not release the liquid when compressed and gave a feeling of a slight dampness upon touching by hand but the hand did not become wet. The gel did not flow, had a strong elasticity, did not collapse readily when pushed, and was highly transparent and uniform.

As a comparative example, a formulation was prepared in the same manner as in Example 1 except that the plasticizer (ethylene glycol) was not blended but water was blended instead to obtain a film-shaped molded product. However, this was less flexible than (a) above, and readily broke when drawn.

Further, as another comparative example, the procedures of Example 1 were repeated except that the hydrophilic polymer (8) was blended instead of the hydrophilic polymer (1) to obtain a liquid-absorbing material (H), which was molded in the manner described above to obtain a film-shaped molded product (h). While this molded product had some flexibility, it broke when drawn. In addition, the surface of the molded product was sticky and, hence, it was difficult to handle it. Furthermore, the liquid absorption magnification of (h) was as large as 262.3 times for water, but the material did not absorb brine so much (15.1 times).

EXAMPLE 9

The liquid-absorbing material composition (B) prepared in Example 2 was coated on nonwoven fabric made of polypropylene using an applicator at a clearance of 0.5 mm. Then, the coated fabric was introduced into a bag made of aluminum-laminate and sealed so that the alcohol and water could not evaporate and heated at 50° C. for 1 day to obtain a sheet-shaped molded liquid-absorbing material (b). When touching by a finger, the finger did not get wetted.

EXAMPLE 10

The liquid-absorbing material composition (C) prepared in Example 3 was coated on a releasing body made of polypropylene using an applicator at a clearance of 1 mm. After it was left to stand at room temperature for 1 hour, the coating was heated at 80° C. for 30 minutes to obtain a sheet-shaped molded liquid-absorbing material (c). This was flexible and did not readily break when drawn.

As a comparative example, the hydrophilic polymer (9) was blended instead of the hydrophilic polymer (3) in Example 3, resulting in that the hydrophilic polymer (9) did not dissolve and uniform sol was not obtained so that molding was impossible.

EXAMPLE 11

The liquid-absorbing material composition (D) prepared in Example 4 was coated on a releasing body made of polypropylene using an applicator at a clearance of 0.5 mm. After it was left to stand at room temperature for 5 hours, the coating was heated at 80° C. for 30 minutes to obtain a sheet-shaped molded liquid-absorbing material (d). This was flexible and did not readily break when drawn.

As a comparative example, the hydrophilic polymer (10) was blended instead of the hydrophilic polymer (4) in

EXAMPLE 4, with the result that the hydrophilic polymer (10) did not dissolve and uniform sol was not obtained so that molding was impossible.

EXAMPLE 12

The liquid-absorbing material composition (E) prepared in Example 5 was coated on a releasing body made of polypropylene using an applicator at a clearance of 0.2 mm. It was left to stand at room temperature for 5 hours to obtain a sheet-shaped molded liquid-absorbing material (e). This was flexible and did not readily break when drawn.

As a comparative example, the hydrophilic polymer (11) was blended instead of the hydrophilic polymer (5) in Example 5, resulting in that the hydrophilic polymer (11) did not dissolve and uniform sol was not obtained so that molding was impossible.

EXAMPLE 13

On the bottom of a metallic vat of a size of 5 cm-deep, 20 cm-long and 20 cm-wide was placed a silicone-coated polyethylene film and the liquid-absorbing material composition (F) prepared in Example 6 was charged thereon. Then, the vat was left to stand at room temperature for 2 days, followed by heating at 50° C. for 1 hour to obtain a film-shaped molded liquid-absorbing material (f). This was flexible and did not readily break when drawn.

As a comparative example, a formulation was prepared in the same manner as in Example 6 except that the water-soluble organic solvent (ethanol) was not blended but water was blended instead for the purpose of obtaining a film-shaped molded product. However, even after 2 days, the composition was in a sol state as confirmed by touching by finger and was not molded.

EXAMPLE 14

The liquid-absorbing material composition (G) prepared in Example 7 was coated on a releasing body made of polypropylene using an applicator at a clearance of 0.5 mm. After it was left to stand at room temperature for 2 hours, the coating was heated at 50° C. for 1 hour to obtain a sheet-shaped molded liquid-absorbing material (g). This was flexible and did not readily break when drawn.

As a comparative example, a formulation was prepared in the same manner as in Example 7 except that water was not blended but isopropyl alcohol was blended instead to obtain a film-shaped molded product. This became amorphous (not in a gel state) when it was attempted to have water absorbed by the resulting molded material and absorbed substantially no water.

What is claimed is:

1. A composition for preparing a liquid-absorbing material comprising:
   a crosslinking agent (component A);
   an N-vinylcarboxamide copolymer (component B) comprising monomer units represented by formula (IA):

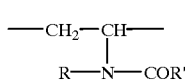

(IA)

wherein R represents a hydrogen atom or an alkyl group having 1 to 4 carbon atom(s) and R' represents an alkyl group having 1 to 4 carbon atom(s), and wherein said N-vinylcarboxamide copolymer includes a functional group which reacts with the component A;

water (component C);
a water-soluble organic solvent (component D); and
a plasticizer (component E);
and wherein the weight ratio of said plasticizer (component E) to said cooolymer (component B) is 1/10–10/1.

2. The composition as described in claim 1, further comprising a hydrophilic polymer (component F) which does not react with the crosslinking agent (component A).

3. The composition as described in claim 1, wherein the weight % ratio of the crosslinking agent (component A) to the N-vinylcarboxamide copolymer (component B) is 0.01–90:99.99–10; wherein the amount of the water (component C) is 10 to 65 % by weight based on the total weight of the composition; and the amount of the water-soluble organic solvent (component D) is 10 to 90% by weight based on the total weight of the composition.

4. The composition as described in claim 1, wherein the crosslinking agent (component A) is at least one crosslinking agent selected from the group consisting of polyfunctional epoxy compounds, aldehydes, N-methylols, dicarboxylic acids, epichlorohydrin, boric acid, diamines, diols, bisepoxides, and diisocyanates.

5. The composition as described in claim 1, wherein the N-vinylcarboxamide copolymer (component B) comprises at least one functional group selected from the group consisting of a hydroxyalkyl group, a carboxyl group, a sulfonic acid group, a phosphoric acid group, an aminocarbonyl group, an amino group, and a mono- or dialkylamino group.

6. The liquid-absorbing material composition as described in claim 1, wherein the N-vinylcarboxamide copolymer (component B) comprises a repeating unit selected from the group consisting of formulae (I)–(IV): formula (I):

(I)

wherein R represents a hydrogen atom or an alkyl group having 1 to 4 carbon atom(s) and R' represents an alkyl group having 1 to 4 carbon atom(s); formula (II):

(II)

wherein $R^1$ represents a hydrogen atom or a carboxyl group or its alkali salts, $R^2$ represents a hydrogen atom, a methyl group or a carboxyl group or its alkali salts, $X^1$ represents a carboxyl group or its alkali salts, or $R^1$ and $X^1$ taken together with the carbon atoms to which they are attached form a cyclic acid anhydride structure; formula (III):

(III)

wherein $R^3$ and $R^4$ independently represent a hydrogen atom, a 1 to 4 carbon alkyl group or a carboxyl group or its alkali salts, A is a group represented by formula (V), (VI) or (VII):

—$R^{51}$—  (V)

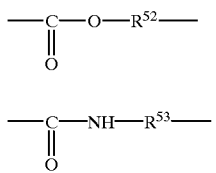

(VI)

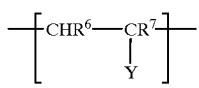

(VII)

wherein $R^{51}$, $R^{52}$, $R^{53}$ independently represent a 1 to 10 carbon straight chain or branched alkylene group, $X^2$ represents a carboxyl group, a phosphoric group or their alkali salts, or $R^3$ and $X^2$ taken together with the carbon atoms to which they are attached form a cyclic acid anhydride structure; and formula (IV):

$$-\!\!\left[\mathrm{CHR}^6-\mathrm{CR}^7_{\phantom{1}Y}\right]\!\!-$$

(IV)

wherein $R^6$ and $R^7$ independently represent a hydrogen atom or a 1 to 4 carbon alkyl group, Y represents a 1 to 4 carbon hydroxyalkyl group, —$CH^2NR^8R^9$, where $R^8$ and $R^9$ independently represent a hydrogen atom, a 1 to 4 carbon alkyl group or a 1 to 4 carbon alkenyl group, —$COOR^{10}$ where $R^{10}$ represents a 1 to 4 carbon alkyl group or a 1 to 4 hydroxyalkyl group, —$CONR^{11}R^{12}$ where $R^{11}$ and $R^{12}$ independently represent a hydrogen atom, a 1 to 4 carbon alkyl group, a 3 to 5 carbon alkenyl group or a methylol group, —$CONH$—$R^{13}$—$NR^{14}R^{15}$ where $R^{13}$ represents a simple chemical bond or the same group as defined by A above, and $R^{14}$ and $R^5$ independently represent the same groups as $R^{11}$ and $R^{12}$ above, or their quaternary ammonium salts, or a phenyl group substituted with 1 to 3 hydroxyl groups at the nucleus thereof; and wherein the weight % ratio of the repeating unit (I) to the repeating units (II), (III) and (IV) is 99.99–50:0.01–50.

7. The composition as described in claim 6, wherein R is a hydrogen atom and R' is a methyl group in formula (I) which represents the repeating unit of the N-vinylcarboxamide copolymer (component B).

8. The composition as described in claim 1, wherein the plasticizer (component E) is a polyhydric alcohol.

9. A molded product of liquid-absorbing material obtained by molding the composition as described in claim 1.

10. The molded product of liquid-absorbing material as described in claim 9, molded into any one of film, sheet, powder, flake or fiber shape.

11. A method of manufacturing a molded product of liquid-absorbing material, comprising molding the composition described in claim 1 into a desired shape and evaporating the water (component C) and the water-soluble organic solvent (component D).

12. The molded product as described in claim 9, wherein said product is a freshness-retaining agent, a moisture-conditioning agent, an agricultural and horticultural water-retaining sheet, a soil improving agent, an anti-dewing agent, a sanitary good, a waste liquid solidifying material, a water preventing sheet, a water running preventing shielding material, a pharmaceutical, a medical tool, a humectant or a desiccant.

* * * * *